United States Patent [19]

Wilkes

[11] 4,096,191
[45] Jun. 20, 1978

[54] HYDROFORMYLATION OF OLEFINS USING AZOXY-DENTATED LIGANDS

[75] Inventor: John B. Wilkes, Richmond, Calif.

[73] Assignee: Chevron Research Company, San Francisco, Calif.

[21] Appl. No.: 479,345

[22] Filed: Jun. 14, 1974

Related U.S. Application Data

[60] Continuation of Ser. No. 150,862, Jun. 1, 1971, abandoned, which is a division of Ser. No. 857,547, Sep. 12, 1969, Pat. No. 3,647,845.

[51] Int. Cl.$^2$ ............................................. C07C 27/22
[52] U.S. Cl. ...................... 260/632 HF; 260/604 HF; 423/417
[58] Field of Search .................. 260/632 HF, 604 HF

[56] References Cited

U.S. PATENT DOCUMENTS

| | | | |
|---|---|---|---|
| 2,576,113 | 11/1951 | Hagemeyer | 260/638 HF |
| 3,033,214 | 5/1962 | Bersworth | 260/534 E |
| 3,231,621 | 1/1966 | Slough | 260/632 HF |
| 3,278,612 | 10/1966 | Greene | 260/632 HF |
| 3,555,098 | 1/1971 | Olivier et al. | 260/632 HF |
| 3,576,881 | 4/1971 | Senn | 260/632 HF |
| 3,594,425 | 7/1971 | Brader et al. | 260/632 HF |
| 3,624,158 | 11/1971 | Deffner et al. | 260/632 HF |
| 3,631,111 | 12/1971 | Tucci | 260/632 HF |
| 3,725,483 | 4/1973 | Deffner et al. | 260/632 HF |

*Primary Examiner*—Joseph E. Evans
*Attorney, Agent, or Firm*—D. A. Newell; John Stoner, Jr.; W. Keith Turner

[57] ABSTRACT

At a temperature in the range 100° C. to 225° C. the destructive dissociation of cobalt carbonyl compounds to cobalt metal and residue is inhibited by the action of one or more azoxy-dentated chelation ligands.

4 Claims, No Drawings

HYDROFORMYLATION OF OLEFINS USING AZOXY-DENTATED LIGANDS

This is a continuation of application Ser. No. 150,862, filed June 1, 1971, now abandoned, which is a division of application Ser. No. 857,547, filed Sept. 12, 1969, now U.S. Pat. No. 3,647,845.

FIELD OF INVENTION

This invention relates to cobalt carbonyl compounds. More particularly, it relates to a method for the stabilization of cobalt carbonyl complex compounds by inhibiting their dissociation into metallic cobalt and residual components. The inhibition results from the action of an added azoxy-dentated chelation ligand. Still more particularly, it relates to the use of the foregoing stabilization method in the production of alcohols and/or aldehydes from olefinically unsaturated compounds by the cobalt carbonyl catalyzed addition of carbon monoxide and hydrogen to the carbon-to-carbon unsaturation linkage(s) of these unsaturated compounds.

BACKGROUND OF INVENTION

Cobalt carbonyl compounds including dicobalt octacarbonyl, cobalt hydrocarbonyl etc. as such or in modified forms are known for their use as catalysts for a variety of reactions relating to olefinic unsaturated organic compounds including the hydroformylation (oxonation) of olefins, isomerization of olefins, carbonylation of amines and aromatic nitriles, hydrosilation of olefins and the like. These catalyst complex are subject to substantial limitations in that unless carbon monoxide pressures in excess of equilibrium values are maintained in their presence, these compounds destructively dissociate into cobalt metal and residue. Catalystic activity is thus lost and cobalt metal is plated-out on reactor walls and associated transfer piping. From time to time the accumulated metal must be removed by a suitable means, often by the use of aqueous nitric acid or a similar undesirably corrosive and inconvenient agent.

It is therefore an object of the present invention to provide a method for the stabilization of cobalt carbonyl complex compounds, thereby substantially reducing cobalt metal deposition on the surfaces of reaction vessels and associated lines.

Another object of the invention is to provide a method for the stabilization of cobalt carbonyl complex compounds thereby permitting their effective use as catalysts at lower carbon monoxide pressures and at higher temperatures than may be satisfactorily employed under conventional hydroformylation reaction conditions.

Another object of the invention is to provide a method to inhibit the plating-out of cobalt metal on the surfaces of a system containing cobalt carbonyl complex compounds from the destructive dissociation of cobalt carbonyl complex compounds.

Still another objective is the provision of an improved hydroformylation process in which alcohol is produced in a single stage process by the reaction of an olefinic hydrocarbon with carbon monoxide and hydrogen in the presence of a cobalt carbonyl catalyst and facilitated by added azoxy-dentated chelation ligands. Other objects and advantages of the present invention will become apparent from the ensuing detailed description thereof.

THE INVENTION

In accordance with the present invention the stability of cobalt carbonyl complex compounds in a system in the presence of carbon monoxide gas is improved at a temperature in the range of from about 100° C. to 225° C. by the addition of an organic azoxy-dentated chelation ligand. For each mol of cobalt at least about $10^{-4}$ mol of the ligand should be available for contact with the complex compound.

In a more particular aspect of the invention, organic compounds containing olefinic unsaturation are converted to saturated alcohols and/or aldehydes having at least one more carbon atom than the precursor olefinic compounds by the reaction of the compound in the liquid phase with carbon monoxide and hydrogen in a reaction system in which the above described stabilized cobalt carbonyl complex compounds are employed as the catalyst. In a corollary aspect of the invention the plating-out of cobalt metal on the surfaces of systems containing the aforementioned cobalt carbonyls is inhibited by the addition of the above described ligands.

Surprisingly, when cobalt carbonyl complex compounds are in contact with the subject ligands, destructive dissociation of the cobalt compound to metal and residue is markedly inhibited at a temperature within the above noted range, and carbon monoxide pressures below conventional equilibrium pressures can be employed with little or no deposition of cobalt metal. Thus, in the presence of the subject ligands hydroformylation reactions at elevated temperatures can be affected at considerably lower pressures than are otherwise required. This permits substantial economies of plant construction and operation. A further advantage of the subject process over the art accrues in that in conventional hydroformylation practice, the hydrogenation of aldehyde to alcohol is inhibited by the necessarily high carbon monoxide partial pressures. The subject azoxy-dentated ligands permit such a substantial reduction in the carbon monoxide partial pressure of the reaction system that both hydroformylation and hydrogenation can be accomplished in a single reactor and/or with but a single catalyst system.

A further advantage arising from the presence of the subject ligands in a cobalt carbonyl-containing system is that such cobalt metal as may be formed does not plate-out on the contiguous surfaces of the system, but is found in general in the form of a loose free flowing powder which is slurried in liquid reactant and product mixtures.

As used herein, the term "complex compound" relates to combinations of two or more atoms, ions, or molecules which arise as a result of the formation of a bond(s) by the sharing of a pair(s) of electrons originally associated with only one of the components, and the complex possesses some identifiable physical or chemical characteristics of a distinct species.

By an azoxy-dentated chelation ligand is meant by definition, as used herein, an organic compound containing the functional grouping

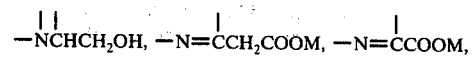

-continued

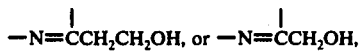

where M is hydrogen, or an alkali metal, alkaline earth metal or ammonium cation and the open valences of the formulas are satisfied by bonds to hydrogen, oxygen or carbon radicals. Organic compounds containing these functional chelation groupings are capable of forming 5 or 6 membered heterocyclic rings with cobalt as follows:

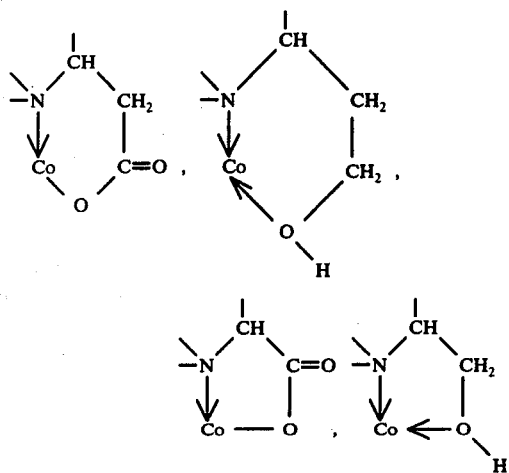

or the analogous structures where there is a carbon nitrogen double bond, for example

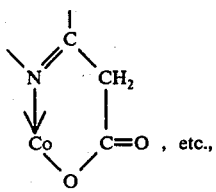

where the arrows connote electron pair sharing between the donor atoms, oxygen or nitrogen, and the donee atom, cobalt, and the open valences are satisfied as noed above.

The azoxy-dentated ligands of the present invention contain at least one oxygen-nitrogen containing azoxy-ligand functional group and by reason of the above prescribed atomic arrangement are capable of forming a bidentate coordination complex, a chelate, in which a cobalt atom is a member of a heterocyclic ring. The atoms of the oxygen-nitrogen pair each have at least one free pair of electrons (i.e., non-bonded electron pair) which are shared in the formation of the chelate. Organic compounds in general having the aforementioned configuration are suitable azoxy-dentated ligands useful for the stabilization of cobalt carbonyl complex compounds within the above noed temperature range and in the presence of carbon monoxide.

Azoxy-dentated ligands having a substantial standard cobalt-ligand association constant are especially useful for the subject stabilizations and are preferred, particularly where they are composed of carbon, hydrogen, oxygen, and nitrogen. On the other hand, azoxy-dentated ligands may contain additional elemetns, that is, where one or more hydrogen atoms bonded to carbon of the compound other than carbon contained in the azoxy functional chelation grouping noted above, are replaced by inert substituent groups, that is non-chelating (i.e., located outside of the bidentate functional grouping, as defined above) hydroxyl, carboxyl, ether, ester, keto, or aldehyde functional groups; non-chelating nitrogen groups as amino, imino, nitrilo, and amide groups; halogen groups as fluoride, bromide, and chloride; and sulfone, sulfoxide and sulfonate.

Surprisingly, azoxy-dentated ligands need not be soluble in the system containing the cobalt carbonyl compound. However, better results in general are obtained when these ligands have an appreciable (at least about 0.01 grams of ligand per 100 grams of the system) solubility at the temperature of the use. Structural considerations, other than the presence of the above prescribed functional chelate grouping for the subject azoxy-dentated ligands, do not pose a functional limitation upon the invention. The compounds contemplated for use herein may be of any structural type so long as they have the prescribed functional chelate grouping, i.e., contemplated compounds may be of any structural type including acyclic, cyclic, polycyclic, heterocyclic and mixed structural variations thereof, and may include carbon skeletons which are saturated, partially saturated, and/or aromatic.

The oxygen atom of the electron pair donor atoms of the functional chelation group of the ligand may be present in any carbon-oxygen functional group. Representative carbon-oxygen functional groups include carbonyl, carboxyl, ester, hydroxyl, ether, aldehyde, and the like groups.

The nitrogen atom of the electron pair donor atoms of the ligand may be present in any trivalent nitrogen-containing functional group in which the nitrogen atom may have single or double bond attachment to other atoms. Representative nitrogen containing functional groups include primary, secondary or tertiary amines, hydroxylamine, imine, and the like.

By a standard cobalt-ligand association constant, as used herein, is meant by definition the constant at 18°–30° C. in a water or a water-dioxane (40:60, respectively) solvent for the equilibrium:

$$Co^{+2} + L^a \rightleftarrows (CoL)^{[+(1)+(a)]}$$

where L is the ligand and $$K = \frac{(CoL)^{[+(1)+(a)]}}{(Co^{+2})(L^a)}$$

(The mixed solvent is required for ligands having little or no water solubility at the standard temperature) where L is the ligand, $a$ is the charge $(0, 1, -1)$ value of the ligand.

By a substantial cobalt-ligand association constant is meant a value for log K (units are liter mol$^{-1}$) as follows:

(1) for a wholly aqueous solvent a value of at least 4
(2) for a 60–40 dioxane-water medium a value of at least 7.

For representative data and background information see "Stability Constants of Metal-Ion Complexes" by L. G. Sillen and A. E. Martell, Special Publication No. 17, London; The Chemical Society, Burlington House, 1964.

The stability of cobalt carbonyl complex compounds which are free of cobalt-phosphorous bonds and of cobalt-metal bonds, other than cobalt-cobalt bonds, are in general improved by the method of the instant invention. Especially advantageous is the use of the present method for the stabilization of dicobalt octacarbonyl, cobalt hydrocarbonyl, and tetracobalt dodecacarbonyl, i.e., cobalt carbonyl complex compounds and the systems tending to equilibrate which result where mixtures of these materials and carbon monoxide gas are at temperatures in the range from about 100° C. to about 225° C.

The cobalt-containing complexes which are stabilized by the instant method can be prepared by known methods. In this preparation, the subject azoxy-dentated ligands may be present during the generation of the cobalt carbonyl complex compound or subsequent thereto. In general, better results in terms of stabilization effects obtain when these ligands are present initially. Normally these complexes are formed in situ by the reaction of cobalt oxide, a cobalt salt or soap with hydrogen and carbon monoxide at elevated temperatures and pressures in a reaction in which a mixed species of carbonyls appear to be formed including dicobalt octacarbonyl, cobalt hydrocarbonyl and a cobalt salt, $Co[Co(CO)_4]_2$. The mixture tends to equilibrate between these species and at a lower rate, in the absence of the subject ligands, with cobalt metal. The mechanism of the present stabilization may actually be a kinetic hindrance of the latter stage. The medium for the in situ preparation in general comprises a liquid reactant, for example, an unsaturated organic compound or an olefinic hydrocarbon, from a reaction system for which the cobalt carbonyl complex is to serve as a catalyst. Inert liquid media or diluents such as saturated hydrocarbons, aromatic hydrocarbons, alcohols, high-boiling reaction byproducts, etc., as known in the art, may also be employed.

The amount of the subject azoxy-dentated ligands which should be present for satisfactory results varies and in general appears to be functionally related to the cobalt ligand association constant. That is, for a given stabilization (time-temperature and corresponding degree of cobalt metal formation) a smaller amount of a ligand having a high association constant will be required for satisfactory stabilization than of a ligand having a relatively lower association constant. The azoxy-dentated chelation ligands preferred for use in the present invention have a cobalt-ligand association constant, water medium, of at least about $10^4$ liter $mol^{-1}$, or, 60–40 dioxane-water medium of at least about $10^7$ liter $mol^{-1}$, or corresponding values for other organic solvent media. In general, the stabilizing effect increases as the association constant becomes larger.

The relative amount of the added azoxy-dentated ligand which should be present varies. Usually even a trace, i.e., of the order of $10^{-4}$ mols per atomic weight of cobalt, is helpful. However, as a practical matter, in general at least about 0.001 mol of the ligand per mol of cobalt in the cobalt carbonyl complex compound should be added. Satisfactory amounts of the ligand are in general in the range below about 5 mols of ligand per mol of cobalt. Excellent results are usually experienced when for each mol of cobalt there is present in the system an amount of the ligand in the range below about 0.5 mol. Larger amounts of added ligand may be desirable where the ligand has a relatively small association constant. Ordinarily, the use of amounts of the ligand in excess of 2 mols per mol of cobalt is undesirable for reasons of relative inefficiency, cost and the like. Usually, better results obtain when the mol ratio is substantially less than stoichiometric, i.e., is in the range 0.1–0.25 to 1.

Representative azoxy-dentated ligands useful in the practice of this invention includes ethylenediamine-N,N,N',N'-tetraacetic acid (EDTA); N'-(2-hydroxyethyl)-ethylenediamine-N,N,N'-triacetic acid (HEDTA); N,N'-di-(2-hydroxyethyl)ethylenediamine-N,N'-diacetic acid; trans-1,2-cyclohexylenedinitrilotetra acetic acid; alkyl, aryl, or aralkyl substituted EDTA compounds, such as N-benzylethylenediaminetriacetic acid; N-butylethylenediaminetriacetic acid; N-cyclohexylethylenediaminetriacetic acid; N,N'-dimethylethylenediaminediacetic acid; ethylenediamine-N,N'-dipropanoic acid; diethylenetriamine-N,N,N,N'N''-pentaacetic acid; ethylenediamine-N,N,N'N'-tetrapropionic acid; the carboxylic acid esters and mixed acid-esters of the foregoing, as well as the salts of the foregoing acids, particularly their salts with tertiary or heterocyclic amines such as pyridine, as well as with ammonium, alkali metal or alkaline earth metal cations, e.g., the ethylenediamine carboxylic acids, salts and esters containing from 1 to 5 azoxy-dentate functional groups, and the like azoxy-dentated ligands.

Other representative azoxy-dentated ligands include nitrilotriacetic acid (NTA); iminodiacetic acid; N-methylaminodiacetic acid; β-hydroxyethyliminodiacetic acid; N-(2-hydroxyethyl)-glycine; N,N-bis(2-hydroxyethyl)-glycine; β-alanine-N,N-diacetic acid; aniline-N,N-diacetic acid; N,N-(diacetic acid)-2-aminobenzoic acid; α-aminobutyric acid; α-amino-α-methylpropionic acid; glutamic acid; 1-aminocyclopentane carboxylic acid; iminodipropionic acid; 1-amino-2-propanone-N,N-diacetic acid; 1-aminocyclohexane carboxylic acid; N-(carboxymethyl) iminodipropionic acid; N-(2-hydroxyethyl)-iminodipropionic acid; N,N-di-(2-hydroxyethyl)-glycine; hexamethylenediamine-N,N,N',N'-tetraacetic acid; and the like compounds.

Still other representative azoxy-dentated ligands, that is non-acidic azoxy-dentated ligands, useful in the present invention includes N,N,N',N'-tetra-(2-hydroxyethyl)-ethylenediamine; N,N,N',N'-tetra-(2-hydroxypropyl)-ethylenediamine; N,N'-di-(2-hydroxyethyl)-ethylenediamine; 2-hydroxymethylpyridine; 8-hydroxyquinoline; 8-hydroxy-2-methylquinoline; o-aminophenol; N-(3-aminopropyl)-diethanolamine; the salts as above of the foregoing, especially with the higher ($C_5$–$C_{20}$) carboxylic acids, i.e., fatty acids; also including the salts of the azoxy-dentate type acids of the preceding paragraphs with the non-acidic azoxy-dentated ligands; and the like.

Yet further representative azoxy-dentated ligands include 2,2'-hydroxyphenylimidazoline; pyridine-2-carboxylic acid; pyridine-2,6-dicarboxylic acid; trans-piperazine-2,3-dicarboxylic acid; piperazine-2,5-dicarboxylic acid; piperazine-2,6-dicarboxylic acid; piperidine-2,6-dicarboxylic acid; 8-hydroxyquinoline; 2-aminomethylpyridine-1-acetic acid; 2,2'-hydroxyphenylimidazoline; quinoline-2-carboxylic acid; 4,4'-ethylenediiminodi-(pentane-2-one); 4(phenylimino)-pentane-2-one; salicylanilide; salicylaldoxime; bis-(salicylidene)-o-phenylenediamine; methylglyoxime; dimethylglyoxime; and the like.

Representative azoxy-dentated ligands containing one or more non-interfering, i.e., inert, substituents includes β-aminoethylsulfonic acid-N,N-diacetic acid; 3-sulfoaniline diacetic acid; 4-hydroxypyridine-2,6-dicarboxylic acid; 3-hydroxyanthranilic acid; 5,7-dichloro-8-hydroxyquinoline; 5-chloro-8-hydroxyquinoline; 8-hydroxyquinoline-5-sulfonic acid; 5-cyano-8-hydroxyquinoline; 4-chloro-2-aminobutyric acid; 1-amino-3-fluorocyclohexane carboxylic acid; 3-methoxyaniline-N,N-diacetic acid; and the like compounds.

The following azoxy-dentated ligands are particularly effective cobalt carbonyl complex compound stabilizers and are also preferred for reasons of cost and availability: (1) N-(2-hydroxyethyl)-ethylenediamine-N,N',N'-triacetic acid; (2) N,N,N',N'-tetra-(2-hydroxyethyl)-ethylenediamine; (3) N,N,N',N'-tetra-(2-hydroxypropyl)-ethylenediamine; (4) N-(3-aminopropyl)-diethanolamine; (5) 8-hydroxyquinoline. The salts of (1) with (2) or (3) are very convenient ligand systems and effective.

In accordance with the invention and in a particular aspect thereof alcohols and/or aldehydes are prepared by the hydroformylation of olefinic compounds by intimately contacting the latter in the liquid phase with hydrogen and carbon monoxide in a reaction under defined conditions of temperature and pressure, catalyzed by complex cobalt carbonyl compounds and stabilized by the presence of added azoxy-dentated ligands.

The principal effect of the presence of the azoxy-dentated ligands of the invention upon cobalt carbonyl complex compounds is that of inhibiting their destructive dissociation with the formation of cobalt metal. Little or no interference with the normal catalytic action of cobalt carbonyl compounds occurs from the presence of the added ligands. Thus, in general, in the employment of the stabilized cobalt carbonyls of the invention the conditions which are satisfactory, as known in the art, are also satisfactory herein. For example, in olefin hydroformylations, suitable reaction temperatures are in the range 100°–225° C., preferably from about 125° to about 200° C. Suitable catalyst-to-feed ratios may vary widely and preferably are varied to achieve, where possible, a substantially homogenous reaction mixture. Catalyst concentrations, based upon olefins feed (weight percentages) and calculated as cobalt metal in the range 0.05 to 5.0 weight percent are usually satisfactory. Preferred amounts ordinarily are in the range 0.1 to 0.5.

At elevated temperatures, cobalt carbonyl compounds are normally maintained by subjecting them to substantial partial pressures of carbon monoxide. These pressures may be satisfactorily employed in the instant invention, but in general the stabilizing action of the subject oxygen-dentated ligands markedly lowers the partial pressure of carbon monoxide required for this purpose. Thus, for the present process, system pressures may vary from about 50 psig at temperatures of the order of 75° C. up to as much as 4000–5000 psig at temperatures of the order of 225° C.

The ratio of hydrogen to carbon monoxide charged may vary widely. Usually, a mol ratio of hydrogen to carbon monoxide in the range 0.5–10 to 1, respectively, is satisfactory. The range 1–3 to 1 is preferred. The synthesis gas (from the partial combustion of natural gas or naphtha) of commerce is a particularly useful mixture.

Olefinically unsaturated organic compounds as known in the hydroformylation (oxo) art are, in general, satisfactory feeds for use in the present invention. Preferred feeds are mono-olefinic hydrocarbons. Of these, linear olefins of the $C_3$ to $C_{20}$ range, propylene oligomers and the like, are the most desirable feeds. Where branched chain olefins are used for the production of oxo-alcohols, it is often more advantageous to effect the carbon monoxide-hydrogen addition to the olefinic double bond at about 140°–170° C. and to subsequently raise the reaction mixture to a higher tmeperature (180°–210° C.) where the reduction of the aldehyde group proceeds more favorably.

Representative olefinic hydrocarbons suitable for use herein include ethene, propene, 1-hexene, 3-heptene, 4-octene, cyclohexene, betapinene, alpha-pinene, 2-heptene, 3-ethylpentene-1, 2-methylpentene-2, cyclopentene, 2(n-propyl)pentene-1, diisobutylene, propylene trimer, codimer heptenes, vinylcyclohexene, cyclododecene, 3-eicosene, 1-dodecene, and the like olefinic hydrocarbons.

COBALT CARBONYL STABILITY TEST

The stabilizing action of azoxy-dentated ligands upon complex cobalt carbonyl compounds is shown by means of a suitable test. The relative stabilizing action upon these carbonyl compounds is shown by subjecting them to a standard set of conditions with and without the added ligand. These conditions include:

| | |
|---|---|
| Temperature, ° C. | 190 |
| Time, hrs. | 6 |
| Solvent | Mixed alcohol-alkane |
| $H_2$:CO mol ratio | 2:1 |
| Pressure, psig | 1600–1800 |

The test is carried out in a stainless steel rocking autoclave having a glass liner. Under the test conditions cobalt salts such as cobalt 2-ethylhexanoate are rapidly converted to complex cobalt carbonyls. Therefore, as a matter of convenience, the salt rather than the carbonyl compound is charged to the autoclave. After the six hours at temperature with agitation, the autoclave and contents is cooled to room temperature and vented. The solution is then filtered and analyzed for cobalt carbonyl by infrared absorption at about 2041 $cm^{-1}$. Metallic solid if present and its form is noted. In the absence of stabilizers and under the test conditions all of the cobalt carbonyl is converted to a cobalt metal plate which is found adhering to the walls of the glass liner and autoclave. In the presence of an effective stabilizer, little or no metal plating-out occurs, or but small amounts of filterable metal powder are formed. With stabilizers of intermediate effectiveness, little or no metal is found in the liner; but metal may be found outside the liner, either deposited on the external liner wall or the autoclave wall, or loosely lodged between the liner and the autoclave wall. Decompositions outside the liner appear to be due to the higher temperatures which exist at the autoclave wall because of the proximity of the heating element and the low level of the stabilizer. The stabilizer inhibits decomposition of the cobalt carbonyl in the solution inside the liner, but does not prevent some diffusion through the vent holes in the liner into the void between the liner and the autoclave inner wall. In Table 1 below is listed a number of representative stability test results.

TABLE I

| EX. NO. | LIGAND USED | WT % OF[1] SOLUTION | MOLS PER MOL COBALT | CONDITIONS[2] PRESSURE[3] PSIG | TIME, HOURS | % OF COBALT AS $CO_2(CO)_8$ | LOG STANDARD LIGAND-COBALT ASSOC. CONSTANT | OBSERVATIONS |
|---|---|---|---|---|---|---|---|---|
| 1 | None | — | — | 1500 | 6 | None | — | All Metal Plated Out |
| 2 | None (0.16g Pyridine Added) | — | — | 1800[4] | 6 | None | — | All Metal Plated Out |
| 3 | $(NCH_2CH_2N)(CH_2CO_2H)_4$ | 0.143 | 0.1 | 1700 | 6 | 25 | 16.1 | Metal Powder Outside Liner |
| 4 | $(NCH_2CH_2N)(CH_2CHOHCH_3)_4$ | 0.236 | 0.085 | 1840 | 10 | 67 | 6.33 | Trace of Metal |
| 5 | $(NCH_2CH_2N)(CH_2CHOHCH_3)_4$ | 0.236 | 0.25 | 1330 | 6 | 72 | 6.33 | Some Metal Powder |
| 6 | 8-HYDROXYQUINOLINE | 0.145 | 0.25 | 1700 | 6 | Trace | 9.1 | No Metal; Probably $[Co(CO)_4-]$ |
| 7 | $(NCH_2CH_2N)(CH_2CH_2OH)_4$ | 0.236 | 0.25 | 1600 | 6 | 43 | 5.04 | Some Red Oil; No Metal $[Co(CO)_4-]$ |
| 8 | $(NCH_2CH_2N)(CH_2CH_2OH)_2$ | 0.047 | 0.05 | 1700 | 17 | 27 | 5.04 | Trace Metal Powder |
| 9 | $(NCH_2CH_2N)(CH_2CH_2OH)_4$ | 0.236 | 0.05 | 1330 | 6 | 45–55 | 5.04 | No Metal Inside Liner; Metal Plate Outside |
| 10 | $(NCH_2CH_2N)(CH_2CH_2OH)(CH_2CO_2H)_3$ | 0.05 | 0.046 | 1020 | 6 | 64 | 14.4 | Metal Plate at One Spot |
| 11 | $(NCH_2CH_2N)(CH_2CH_2OH)(CH_2CO_2H)_3$ | 0.05 | 0.046 | 1300 | 6 | 96 | 14.4 | Trace Red and Grey Solids |
| 12 | $(NCH_2CH_2N)(CH_2CH_2OH)(CH_2CO_2H)_3$ | 0.05 | 0.046 | 1670 | 17 | 49 | 14.4 | No Metal, Red Solids Present |
| 13 | $(NCH_2CH_2N)(CH_2CH_2OH)(CH_2CO_2H)_3$ | 0.05 | 0.046 | 1700 | 6 | 52 | 14.4 | No Metal, Red Solids Present |
| 14 | $(NCH_2CH_2N)(CH_2CH_2OH)(CH_2CO_2H)_3$ | 0.01 | 0.009 | 1730 | 6 | 60 | 14.4 | Metal Powder in Liner |
| 15 | $(NCH_2CH_2N)(CH_2CH_2OH)(CH_2CO_2H)_3$ | 1.08 | 1.0 | 2230 | 8 | None | 14.4 | No Metal Red Crystals |

[1]Solvent: 50g n-heptane plus 50g $C_{12}$–$C_{15}$ oxo-alcohol; all runs with 0.236g of cobalt as octanoate
[2]Temperature 190° C.
[3]$H_2$:CO mol ratio 2:1
[4]$H_2$:CO ratio 1.3:1

The above examples demonstrate that azoxy-dentated ligands stabilize cobalt carbonyl complex compounds. Substantial inhibition of thermal destructive dissociation of these compounds to metal and residue is shown and such metal as may be produced is mainly in the form of a loose powder rather than plated-out upon portions of the walls of the containing system. Thus, although carbon monoxide partial pressures may be as much as 2200 pounds below the carbon monoxide pressure required for maintaining cobalt carbonyl complex compounds in the absence of the azoxy-ligand, the presence of the subject ligands in contact with the carbonyl compounds inhibits their dissociation.

Even where the stabilizing action of the azoxy-ligand may not be sufficient to maintain at least some cobalt carbonyl values in the system after six hours of the above severe test conditions, nevertheless the presence of the ligand has a useful and salutary effect. Ordinarily in the use of cobalt carbonyl compounds, reaction times are less than six hours and azoxy-ligand stabilizers which are not effective under the above severe six hour test are in fact satisfactory inhibitors. A further advantage resulting from the use of the azoxy-dentate ligands as demonstrated by the examples is that such cobalt metal as may be produced is in the form of a loose metal powder rather than in the form of an adhering plated-out film upon portions of the reaction system surface.

As shown in subsequent examples which further illustrate the present invention, the presence of the instant azoxy-ligands permits the effective use of cobalt carbonyl complex compounds in reaction systems having a reduced carbon monoxide partial pressure.

EXAMPLES 15–17

Some of the advantages of the subject process, including the inhibition of metal deposition, are illustrated by comparative examples in which $C_{13}$–$C_{14}$ α-olefin feeds are converted to oxo alcohols in a cobalt carbonyl catalyzed hydroformylation using accepted commercial catalyst requirements, e.g., 0.2–0.5 weight per cent of cobalt based upon olefin and other conditions, as noted in Table II below.

TABLE II

| HYDROFORMYLATION TYPE | NONSTABILIZED CONVENTIONAL | | OXYGEN-DENTATED LIGAND STABILIZED |
|---|---|---|---|
| EXAMPLE | 15 | 16 | 17[a] |
| HYDROFORMYLATION CONDITIONS | | | |
| TEMP., ° C. | 175 | 200 | 190 |
| PRESSURE, PSIG | 3500 | 4400 | 2090 |
| CARBON MONOXIDE | 1550 | 3000 | 700 |
| HYDROGEN | 1850 | 1400 | 1390 |
| TIME, MIN. | — | 180 | 130 |
| HYDROGENATION CONDITIONS | | NOT NEEDED | NOT NEEDED |
| TEMP., ° C. | 140 | — | |
| PRESSURE, PSIG | 1400 | — | |
| YIELDS, WT % OF FEED OLEFIN | | | |
| ALCOHOL | 82 | 85 | 84 |
| PARAFFIN | 8 | 12 | 9 |
| THICK OIL | 16 | 10 | 7 |

[a]Ligand used was N-(2-hydroxyethyl)-ethylenediamine triacetic acid, one mol/mol of cobalt.

Comparative Examples 15–17 demonstrate a particular aspect of the invention. In the absence of the stabilizer ratio of 2:1. The other conditions and results were as noted in Table III.

TABLE III
SINGLE STAGE HYDROFORMYLATIONS

| EX. NO. | AZOXY-LIGAND | COBALT WT % OF OLEFIN [0] | MOLS LIGAND MOL COBALT | CONDITIONS TEMP. °C. | PRESSURE PSIG | TIME MIN. | PRODUCTS, MOL % [1] RCH$_2$OH | RCHO |
|---|---|---|---|---|---|---|---|---|
| 18 | o-Aminophenol | 0.13 | 2 | 207 | 2400 | 120 | 74 | 4 |
| 19 | o-Aminophenol | 0.47 | 0.25 | 190 | 2190 | 120 | 76 | Trace |
| 20 | Salicylaldoxime | 0.47 | 2 | 190 | 2125 | 141 | 76 | Trace |
| 21 | HEDTA[2] | 0.47 | 1 | 190 | 2090 | 130 | 84 | Trace |
| 22 | HEDTA[2] | 0.47 | 2 | 193 | 2130 | 620 | 8 | 43 |
| 23 | ENTOL[3] | 1.2 | 0.04 | 93 | 2140 | 120 | 2 | 81[5] |
| 24 | ENTPROL[4] | 0.25 | 0.5 | 190 | 1800 | 140 | 71 | 2 |

[0] All feeds $_n$—C$_{13}$—1—alkene except for example 24 in which 1-octene was used.
[1] Based upon olefin feed. Balance is paraffin and polymer.
[2] HEDTA is (NCH$_2$CH$_2$N)(CH$_2$CH$_2$OH)(CH$_2$COOH)$_3$
[3] ENTOL is (NCH$_2$CH$_2$N)(CH$_2$CH$_2$OH)$_4$
[4] ENTPROL is (NCH$_2$CH$_2$N)(CH$_2$CH(OH)CH$_3$)$_4$
[5] 92% conversion ers (Example 16), it is necessary that the system pressure be very high; otherwise the catalyst will rapidly dissociate to metallic cobalt with loss of the catalytic activity before the reaction can proceed appreciably. On the other hand, the presence of an azoxy-dentate stabilizer (Example 17) permits use of at least a 50 per cent pressure reduction, i.e., 2090 psig vs. 4400 psig and, the use of a lower reaction temperature. Little or no metallic cobalt is plated-out on the reactor surfaces where the stabilizer is present in the system. Thus, the use of the azoxy-ligand stabilizers permit the employment of less severe operating conditions and/or fewer process stages, and equipment cost savings are substantial.

In addition to the above stabilizers, other representative azoxy-dentated ligands including 4,4'-dimorpholino methane, N,N'-di(2-hydroxy-x-dodecylbenzyl) ethylene diamine, tetraethyl ethylenediamine tetraacetate, oleyl sarcosine, and N-(3-aminopropyl)-diethanolamine were subjected to the above described stability test. The demonstrated stabilization effects ranged from good to excellent with little or no deposition of cobalt occurring inside the bomb liner. On the other hand, when the ligand contained no oxygen, for example diethylenetriamine, ethylenediamine, 1,3-propanediamine, no more than a trace, if any, cobalt carbonyl survived the test and the bulk of the cobalt was plated out as metal on the liner walls.

These data further show that the subject ligands do not materially change the nature of the effective cobalt carbonyl catalyst species in a hydroformylation. It further appears that the action of these ligands in facilitating a hydroformylation reaction is in the nature of inhibiting cobalt metal formation. Cobalt carbonyl catalyzed hydrogenations of oxo aldehydes are favored by high temperatures (180°–200° C. and by low pressures of carbon monoxide. Thus, the presence of the instant ligands permits operation under conditions which permit effective conversion of olefins to alcohols in a single stage or reactor and with excellent yields.

EXAMPLES 18–24

In these examples representative azoxy-dentated ligands were employed for stabilization of the cobalt carbonyl catalysts in the hydroformylation of alkenes. The reactions were carried out in a rocking autoclave using 0.24 grams of cobalt (as carboxylate salt) in heptane diluent and a hydrogen to carbon monoxide mol ratio of 2:1. The other conditions and results were as noted in Table III.

The above examples demonstrate that organic compounds containing the subject azoxy-dentate functional grouping markedly stabilize cobalt carbonyl complex compounds. In these runs there was negligible, if any, formation of cobalt metal. The catalyst conditions at the end of the run with the reaction mixture at room temperature were as follows:

| RUN | CATALYST FORM |
|---|---|
| 18 | Trace of Metal Powder Balance in Solution |
| 19 | No Metal |
| 20 | Clear Solution; No Metal |
| 21 | No Metal; Some Cobalt as Red Crystalline Ppt. |
| 22 | No Metal; Cobalt as Red Crystalline Ppt. |
| 23 | No Metal; Some Cobalt as Complex in Separated Red Oil Phase |
| 24 | No Metal; No Separated Red Oil Phase |

In the absence of the above azoxy-ligands, and under comparable reaction conditions, system pressures must in general be much higher, otherwise conversions and yields of the desired product are unsatisfactory and the cobalt of the catalyst is found to be all, or in substantial part, plated-out on the reactor surfaces in contact with the reaction medium.

The foregoing examples also show that the subject azoxy-dentated ligands are useful as a means of inhibiting the plating-out of cobalt metal onto the surfaces of systems containing cobalt carbonyl complex compounds at temperatures and carbon monoxide partial pressures where destructive dissociation of these complex compounds occurs, e.g., at temperatures in the range from about 50° C. to 25° C. and at pressures in the range from about 1 to 300 atmospheres.

EXAMPLES 25–34

These examples were carried out in the manner as in Examples 18–24 above using the C$_{13}$ olefin feed, unless otherwise noted, except that two temperature stages were used in Examples 26 and 32 and in the first stage the mol ratio H$_2$:CO was 1:1 to 1.2:1, while in the second it was 3:1. In Example 33 a 3:1 mol ratio of H$_2$:CO was used throughout. Other conditions and results are shown in Table IV below.

TABLE IV

| EX. NO. | AZOXY-LIGAND | TWO STAGE HYDROFORMYLATIONS | | | | | PRODUCTS, MOL %[1] | |
|---|---|---|---|---|---|---|---|---|
| | | COBALT WT % OF OLEFIN | MOLS LIGAND MOL COBALT | CONDITIONS | | | | |
| | | | | TEMP. °C. | PRESSURE PSIG | TIME MIN. | RCH$_2$OH | RCHO |
| 25 | 8-HYDROXYQUINOLINE | 0.94 | 0.25 | 93 | 2120 | 180 | | |
| | | | | 191 | 2450 | 90 | 83 | Trace |
| 26 | NTA[2] | 0.47 | 0.25 | 149 | 2000 | 125 | | |
| | | | | 191 | 2250 | 110 | 80 | Trace |
| 26 | EXTPROL[3] | 0.25[4] | 0.05 | 163 | 1300 | 55 | 72 | 0.7 |
| | | | | 190 | 1820 | 65 | | |
| 27 | EDTA[5] | 0.47 | 0.25 | 149 | 2000 | 90 | | |
| | | | | 191 | 2200 | 110 | 80 | Trace |
| 28 | EDTA | 0.94 | 0.25 | 95 | 2070 | 180 | | |
| | | | | 191 | 2360 | 60 | 85 | 2 |
| 29 | HEDTA[6] [10] | 1.2 | 6×10$^{-4}$ | 93 | 2140 | 180 | | |
| | | | | 191 | 2280 | 60 | 77 | 3 |
| 30 | HEDTA[10] | 0.94 | 0.25 | 110 | 1900 | 120 | | |
| | | | | 191 | 2150 | 120 | 83 | 1 |
| 31 | 8-HYDROXYQUINOLINE[10] | 0.94[7] | 0.25 | 82 | 2000 | 260 | 80 | |
| | | | | 191 | 2150 | 90 | | Trace |
| 32 | HEDTA | 0.25[8] | 0.08 | 163 | 1340 | 45 | | |
| | | | | 190 | 1950 | 75 | 73 | 1 |
| 33 | ENTOL[9] | 0.47 | 0.25 | 93 | 2380 | 75 | | |
| | | | | 135 | 2475 | 120 | 84 | Trace |
| 34 | HEDTA | 0.24[11] | 0.11 | 160 | 1400 | 163 | (98 wt.%) | 41 |
| | | | | 188 | 2000 | 191 | | |

[1] Based on Feed and 100% Conversion. Balance RH and Polymer.
[2] NTA is N(CH$_2$CO$_2$H)$_3$.
[3] ENTPROL is (NCH$_2$CH$_2$N)(CH$_2$CH(OH)CH$_3$)$_4$.
[4] Feed was 1-octene.
[5] EDTA is (NCH$_2$CH$_2$N)(CH$_2$CO$_2$H)$_4$.
[6] HEDTA is (NCH$_2$CH$_2$N)(CH$_2$CH$_2$OH)(CH$_2$CO$_2$H)$_3$.
[7] Feed was 1-dodecene.
[8] Feed was branched heptenes from olefin polymer.
[9] ENTOL is (NCH$_2$CH$_2$N)(CH$_2$CH$_2$OH)$_4$.
[10] Co$^{2+}$ converted to Co$_2$(CO)$_8$ by reaction with CO and H$_2$ at higher temperature before addition of olefin.
[11] Feed was 57 wt. % trans-4-octene, 30 wt. % 3-heptenes, and 13 wt. % 1-hexene, in benzene solvent.

The foregoing examples show that azoxy-dentated ligands in general are effective agents for the stabilization of cobalt carbonyl complex compounds. Mol ratios of the ligand to the cobalt of the cabonyl of the compound may vary widely depending upon the particular ligand being used. Ratios small as 6×10$^{-4}$, Example 29, or as high as 2, Example 18, are effective.

In addition to the above described advantages of the present invention, there is a large reaction rate gain in the production of oxo alcohols which is made possible by the presence of the present azoxy-dentated ligands. This effect can be understood from a consideration of the rate equation, for the conversion of aldehydes to alcohols with cobalt carbonyl catalyst:

$$d(ROH)/dt = k(RCHO)(Co)(pH_2)/(pCO)^2$$

The foregoing examples demonstrate that the presence of the azoxy ligand makes possible the employment of lower carbon monoxide partial pressures. Thus, since the hydrogenation reaction rate is inversely proportional to the square of the carbon monoxide pressure, a reduction in this pressure is reflected by large rate gains in the production of the alcohol.

The above examples demonstrate appreciable yield and pressure reduction advantages over the conventional unmodified reaction. Similarly relative advantages of the instant azoxy-dentated ligands over the organo phosphine-type materials are evident. The latter appear to substantially decrease the catalyst activity. Moreover, about 100–150 times more of the organo phosphine is required than for the azoxy-ligand.

HYDROFORMYLATION OF n-ALKENES

Straight chain n-alkanols or isomeric alkanol mixtures containing predominantly n-alkanol are preferred in the art for many uses. In the hydroformylation of straight chain alkenes, e.g., n-x-alkenes where x may connote terminal or internal olefinic unsaturation, the use of the subject azoxy-dentated hydroformylation catalysts results in substantially the conventional product distribution as may be noted from the comparative examples noted in Table V carried out at 177° C.

TABLE V

| Ex. No. | Olefin Feed | Product, % n-1-alkanol | |
|---|---|---|---|
| | | No Ligand | Ligand Added |
| 40 | 1-heptene | 50 | 50 |
| 41 | 2-heptene | 50 | 50 |
| 42 | 3-heptene | — | 50 |

HYDROFORMYLATION OF BRANCHED CHAIN ALKENES

A yet further advantage is notable from the use of the subject azoxy-dentated ligand stabilization of the cobalt carbonyl catalyst where branched chain heptanes are widely used for the production of isooctyl alcohols. Branched chain C$_6$ and C$_8$ olefins are used to make C$_7$ and C$_9$ alcohols, and nonenes from propylene oligomerization are used to make isodecyl alcohol.

TABLE VI

| | | HYDROFORMYLATION OF BRANCHED OLEFINS | | | | | |
|---|---|---|---|---|---|---|---|
| EX. NO. | OLEFIN | COBALT WT % OF OLEFIN | CATALYST STABILIZER | MOLES MODIFIER MOL COBALT | CONDITIONS | | PRODUCT ALCOHOL WT % OF OLEFIN |
| | | | | | TEMP. °C. | PRESSURE PSIG[2] | TIME MIN. | |
| 43 | HEPTENES | 0.25 | HEDTA | 0.08 | 162 | 1340 | 45 | |

TABLE VI-continued
HYDROFORMYLATION OF BRANCHED OLEFINS

| EX. NO. | OLEFIN | COBALT WT % OF OLEFIN | CATALYST STABILIZER | MOLES MODIFIER MOL COBALT | CONDITIONS TEMP. °C. | CONDITIONS PRESSURE PSIG [2] | CONDITIONS TIME MIN. | PRODUCT ALCOHOL WT % OF OLEFIN |
|---|---|---|---|---|---|---|---|---|
| 44 | HEPTENES | 0.25 | NONE | — | 188 / 175 | 1950 / 3500[1] | 75 / 90 | 96 / 94[3] |
| 45 | HEPTENES | 0.5 | OCT$_2$P$\phi$[6] | 2.5 | 185 | 130[4] | 165 | 54 |
| 46 | DIISO-BUTYLENE | 0.25 | HEDTA | 0.04 | 160 / 189 | 1300 / 1900 | 60 / 60 | 77 |
| 47 | DIISO-BUTYLENE | 0.5 | OCT$_2$P$\phi$[6] | 2.5 | 185 / 215 | 1300[4] / 1300[4] | 120 / 120 | 44 |
| 48 | 3-ETHYL-1-PENTENE | 0.26 | HEDTA | 0.09 | 160–168 / 192 | 1450 / 2000 | 120 / 120 | 94 |
| 49 | OCTENES[5] | 0.22 | HEDTA | 0.12 | 160 / 188 | 1450 / 2100 | 60 / 120 | 98 |

[1]Conventional method. Yield after separate hydrogenation of aldehydes.
[2]Where two pressures are shown, initial pressure is at 1:1 H$_2$:CO mol rate, and second pressure at 3:1 H$_2$:CO mol ratio, except as noted.
[3]1.2:1 H$_2$:CO mol ratio.
[4]2:1 H$_2$:CO mol ratio.
[5]Mainly 2-(n-propyl)-pentene-1 and 2-methyl-3-ethyl-pentene-1.
[6]Dioctylphenyl phosphine.

From a comparison of Examples 43–49, it is to be seen that the use of the azoxy-dentate ligands herein in the formylation of branched chain olefins results in substantial advantages, particularly in the case of the diisobutylene-type olefins. The use of only a trace of azoxy ligand results in almost double the alcohol yield compared to the use of a phosphine-type catalyst modifier where especially large amounts of the costly phosphine are required.

AZOXY-DENTATED LIGAND MIXTURES

Mixtures of the subject ligands may be used and can at times be more advantageously employed than an individual ligand. In the following example (NCH$_2$CH$_2$N)(CH$_2$CH$_2$OH)(CH$_2$CO$_2$H)$_3$ was found to have limited solubility or a slow rate of dissolution in the reaction medium. However, when a second ligand (NCH$_2$CH$_2$N)(CH$_2$CH(OH)CH$_3$)$_4$ was mixed with the carboxylic azoxyligand, both readily dissolved into the medium. Possibly there was an acid-base type interaction.

EXAMPLE 50

In a stirred 1 liter autoclave were charged 75 g (0.76 mol) of 3-heptene, 0.36 gram of cobalt (as the octanoate salt), 225 grams of benzene diluent and 0.16 weight per cent, based upon the heptene, of a mixture of the above noted ligands, HEDTA and ENTPROL. The weight ratio of the triacetic acid derivative to the tetranol was 1:5. The reactor and charge was freed of oxygen by a nitrogen purge and heated to 177° C. Carbon monoxide and hydrogen in the mol ratio of 1:2 respectively were charged to the heated reactor to a system pressure of 1300 psig. After an 80 minute reaction period the reactor and contents were cooled to room temperature, e.g., ca 22° C. No cobalt metal deposit was formed. The conversion of the heptene was complete, and based upon the olefin feed the product mixture contained 70 mol per cent of C$_8$ alcohol and 4 mol per cent of C$_8$ aldehyde.

HYDROFORMYLATION-ALDOL CONDENSATIONS WITH AZOXY-LIGAND STABILIZATION

A co-catalyst system comprising a complex cobalt carbonyl hydroformylation catalyst and added manganese is known to be useful for the production of dimer-alcohol. Presumably under the influence of the manganese all or part of the initial aldehyde product from the hydroformylation undergoes an aldoltype condensation product which is hydrogenated to an alkanol under hydroformylation conditions. The subject azoxy-dentated ligands ae effective stabilizers in the foregoing reaction systems.

EXAMPLE 51

A cobalt-manganese hydroformylation aldol condensation co-catalyst was prepared by charging to a 0.3 liter autocalve 2.5 g (0.005 mol) of cobalt octoate (11.8% cobalt), 5.0 g (0.0055 mol) of manganese naphthenate (6% manganese), 37.5 g of benzene and 0.07 g of an azoxy-dentated ligand mixture as in Example 39, except that the ratio of the tetranol to the triacetic acid derivative was 2.5 to 1 respectively. The sealed reactor and contents was heated to about 190° C. and pressured to about 1500 psig with a hydrogen-carbon monoxide mixture having a mol ratio of 2:1. After the cobalt carbonyl complex hydroformylation catalyst was formed (reaction time about 60 min.) the autocalve and contents were cooled and vented to facilitate the charging of 75 grams (0.75 mol) of a C$_7$–C$_8$ 1-alkene mixture (~96% C$_7$). The autocalve was resealed and pressured to 900 psig with an equimolar gaseous mixture of hydrogen and carbon monoxide, and heated to 135° C.–150° C. and a pressure of 1050 psig for a period of 110 minutes. Thereafter, the temperature was raised to 190° C. while the pressure was increased to 1690 psig using hydrogen gas only. Thereafter pressure was maintained at 1690 psig by the addition of a 3:1 mol ratio mixture of hydrogen and carbon monoxide over a period of 90 minutes reaction time. The reactor and resulting product was cooled and vented. No cobalt or manganese metal was detectable in the reactor. The conversion was complete and the product analyzed (distillation and gas-liquid chromatography) as follows:

| Component | Yield, Weight, g |
|---|---|
| C$_8$–C$_9$ alcohols | 52.4 |
| C$_{16}$ aldehyde | 4.2 |
| C$_{16}$ alcohol | 13.0 |
| C$_{17}$ alcohol | 1.2 |
| Total | 60.8 |

A substantial yield of dimer alcohol was produced.

I claim:

1. Process for the addition of a —CH$_2$OH group to a hydroformylatable organic compound containing olefinic unsaturation which comprises reacting said compound with carbon monoxide and hydrogen at a temperature in the range from about 100° C to 225° C in the presence of a hydroformylation catalyst consisting essentially of a cobalt carbonyl complex compound wherein said catalyst is stabilized by the presence of an ethylenediamine carboxylic acid, salt, or ester containing from 1 to 5 azoxy-dentate functional groups selected from a class consisting of

-continued

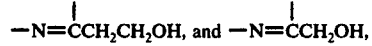

wherein M is hydrogen or an alkali metal, alkaline earth metal or ammonium cation and wherein the open valences of the functional groups are satisfied by bonds to hydrogen or hydrocarbon radicals; and werein the ethylenediamine carboxylic acid, salt, or ester is present in an amount from 0.10 mol to 0.25 mol per mol of cobalt.

2. The process as in claim 1 further characterized in that the ligand is N-(2-hydroxyethyl)-ethylenediamine-N,N',N'-triacetic acid.

3. The process as in claim 1 further characterized in that the stabilizer is a ligand salt.

4. The process as in claim 1 further characterized in that the hydroformylatable organic compound is a mono-olefinic hydrocarbon.

* * * * *